(12) United States Patent
Glocker et al.

(10) Patent No.: US 10,357,611 B2
(45) Date of Patent: Jul. 23, 2019

(54) CLOSURE PIECE FOR A POWDER SYRINGE, AND POWDER SYRINGE

(71) Applicant: VETTER PHARMA-FERTIGUNG GmbH & CO. KG, Ravensburg (DE)

(72) Inventors: Joachim Glocker, Weingarten (DE); Tilman Roedle, Wolfegg (DE)

(73) Assignee: VETTER PHARMA-FERTIGUNG GMBH & CO. KG, Ravensburg (DE)

( * ) Notice: Subject to any disclaimer, the term of this patent is extended or adjusted under 35 U.S.C. 154(b) by 0 days.

(21) Appl. No.: 15/865,350

(22) Filed: Jan. 9, 2018

(65) Prior Publication Data

US 2018/0126081 A1 May 10, 2018

Related U.S. Application Data

(63) Continuation of application No. 14/002,580, filed as application No. PCT/EP2012/000787 on Feb. 23, 2012, now Pat. No. 9,943,648.

(30) Foreign Application Priority Data

Mar. 3, 2011 (DE) ........................ 10 2011 013 792

(51) Int. Cl.
*A61M 5/31* (2006.01)
*A61M 5/28* (2006.01)
*A61J 1/14* (2006.01)
*A61M 5/34* (2006.01)
*A61J 1/20* (2006.01)

(52) U.S. Cl.
CPC .............. *A61M 5/31* (2013.01); *A61M 5/284* (2013.01); *A61M 5/286* (2013.01); *A61J 1/1406* (2013.01); *A61J 1/2041* (2015.05); *A61M 5/345* (2013.01); *A61M 5/347* (2013.01); *A61M 2005/287* (2013.01); *A61M 2005/312* (2013.01); *A61M 2005/3104* (2013.01); *A61M 2005/3106* (2013.01); *A61M 2005/3118* (2013.01)

(58) Field of Classification Search
CPC .................. A61J 1/1406; A61J 1/2041; A61M 2005/287; A61M 2005/3104; A61M 2005/3106; A61M 2005/3118; A61M 2005/312; A61M 5/284; A61M 5/286; A61M 5/31; A61M 5/345; A61M 5/347
See application file for complete search history.

(56) References Cited

U.S. PATENT DOCUMENTS 5,069,670 A * 12/1991 Vetter .................... A61M 5/28
604/218

* cited by examiner

*Primary Examiner* — Imani N Hayman
(74) *Attorney, Agent, or Firm* — Stephen T. Olson; Harness, Dickey & Pierce, P.L.C.

(57) ABSTRACT

A closure piece for a powder syringe is proposed, having a main body, a sealing element, which is disposed on the main body such that it rests in a sealing manner against a distal opening of a powder syringe, when the closure piece is disposed in the closing position thereof on the powder syringe, and a channel, which passes through the main body and the sealing element and has a proximal and a distal end. The closure piece is characterized by a retaining element, which is configured and/or can be disposed such that, prior to an activation of the powder syringe, any powder from a chamber of the powder syringe is at least substantially, preferably completely, prevented from penetrating the channel, when the closure piece is disposed in the closing position thereof on the powder syringe.

23 Claims, 9 Drawing Sheets

CLOSURE PIECE FOR A POWDER SYRINGE, AND POWDER SYRINGE

CROSS-REFERENCE TO RELATED APPLICATIONS

This application is a continuation of U.S. patent application Ser. No. 14/002,580 filed on 30 Aug. 2013, which is a 371 U.S. National Stage of International Application No. PCT/EP2012/000787 filed 23 Feb. 2012, which claims the benefit of German Patent Application No. 102011013792.0 filed 3 Mar. 2011. The entire disclosures of each of the above applications are incorporated herein by reference.

DESCRIPTION

The invention relates to a closure piece for a powder syringe according to the preamble of claim 1, as well as a powder syringe according to the preamble of claim 16.

Closure pieces and powder syringes of the presently mentioned kind are known in the art. Dual chamber systems having a proximal and a distal chamber are preferably used as powder syringes. The proximal chamber typically comprises a liquid solvent and is separated from the distal chamber by a central plug, which includes a material that is soluble in the solvent. Said material can be a free-flowing powder. Known closure pieces include a channel that is in communication with the distal chamber, on the one hand, and that can be brought in fluid communication with a cannula or needle of a syringe that is attached to the closure piece, on the other hand. It is possible for powder to enter the area of the closure piece that is provided for the channel and/or into the channel itself. This can cause clumping, meaning the formation of agglomerates of the powder-type material, and the material may no longer be soluble. When this occurs, the channel is blocked such that the dual chamber system is no longer usable. The same problem also exists with a powder syringe that is not configured as a dual chamber system but that includes one closure piece with one channel. Powder agglomerates can form inside the channel in this instance as well, thus blocking the channel.

Therefore, it is the object of the present invention to provide a closure piece for a powder syringe as well as a powder syringe that do not suffer from the aforementioned disadvantages.

The object is achieved by a closure piece having the characterizing features as set forth in claim 1. The closure piece for a powder syringe comprises a main body and a sealing element, with the sealing element being disposed such on the main element that it rests in a sealing manner against a distal opening of a powder syringe, when the closure is disposed in the closing position thereof on the powder syringe. The closure piece also includes a channel that passes through the main body and the sealing element. Said channel includes a proximal and a distal end. The closure piece is characterized by a retaining element that is configured and/or disposed such that, prior to the activation of the powder syringe, any powder coming from a chamber of the powder syringe is at least substantially, preferably completely, prevented from penetrating the channel, when the closure piece is disposed in the closing position thereof on the powder syringe. The wording "at least substantially" means that at most such a powder quantity can penetrate the channel that clumping is still precluded from occurring. The retaining element is configured such that it prevents the penetration of powder-like material into the channel of the closure piece, when said closure piece is disposed in the closing position thereof, or it can—if necessary, also separated from the remaining elements of the closure piece—be disposed such that any penetration of powder into the channel is prevented. The retaining element is preferably disposed such that the incidence of any residual quantities that could still clump is minimized or avoided completely, with the latter being particularly preferred. The retaining element can be, simultaneously, configured correspondingly as well as with the capacity of being disposed correspondingly. The retaining element virtually separates the channel from the powder-containing chamber, such that no agglomerates can form inside the channel blocking the same. The functioning of a powder syringe that is provided with the closure piece is therefore ensured, even over extended storage periods. The position in which the syringe, with the applied closure piece, is stored is immaterial, because, due to the retaining element, powder cannot penetrate the channel irrespective of the respective storage position, or, if at all, only such quantities are able to enter that are insufficient to cause clumping.

A closure piece comprising a closure piece cap for closing the distal end of the channel is preferred, wherein the closure piece cap includes a rod-like projection. Said projection passes through the channel, and wherein the retaining element is provided thereon. The rod-like projection is thus quasi a locking means for the channel. The advantage therein lies in the fact that when the closure piece cap is removed to activate the powder syringe the channel is released at the same time, without any need for further steps. Moreover, a closure piece that already comprises a closure piece cap does not require any further elements.

Also preferred is a closure piece that includes a retaining element that is configured as a slotted membrane. The pressure forces that are generated when activating the syringe and/or releasing the content of the syringe into a patient can burst open and deform the membrane, and the membrane can be perforated by the needle-like device or dilated in the region of the slot in order to release the channel.

Further preferred is a closure piece with a retaining element that is configured as a displaceable element in the direction along the channel. In the storage state of the syringe, said element is disposed quasi at the proximal end of the channel and closes the same. To activate the powder syringe, the element can be displaced along the channel toward the distal end thereof, where it finally exits the channel, thereby releasing the channel.

Also preferred is a closure piece where the retaining element comprises a soluble substance. It is especially preferred for the retaining element to comprise a lyophilized substance. When the syringe is activated, said substance can be dissolved by a solvent, thereby releasing the channel.

Finally, also preferred is a closure piece where the retaining element comprises a closure piece disc that is configured such that the disc has the capacity to rest in a sealing manner against a narrowing of the powder syringe. This way, said disc is able to prevent powder from penetrating into the channel. The closure piece disc can be disposed particularly in the region of the narrowing of the powder syringe in such a manner that, prior to the activation of the powder syringe, no powder is able to penetrate into the channel. When the powder syringe is activated, a closure piece disc is displaced from the narrowing, such that the fluid path to the channel is released.

Further embodiments can be derived from the dependent claims.

The present object is also achieved in that a powder syringe with the characterizing features of claim 16 is provided. Said syringe includes a distal opening and is characterized in that it is provided with a closure piece according to any one of the claims 1 to 15. Due to the closure piece that comprises a retaining element for the powder, the powder syringe can be stored for any length of time and in any position, and without clumping risk involving powder inside the channel, because the powder is held back by the retaining element.

Preferably, the powder syringe is configured as a dual chamber system.

Especially preferred is a powder syringe with a narrowing in the region of the distal end thereof.

The invention will be explained in further detail below based on the drawings. Shown are as follows.

Figure 1:
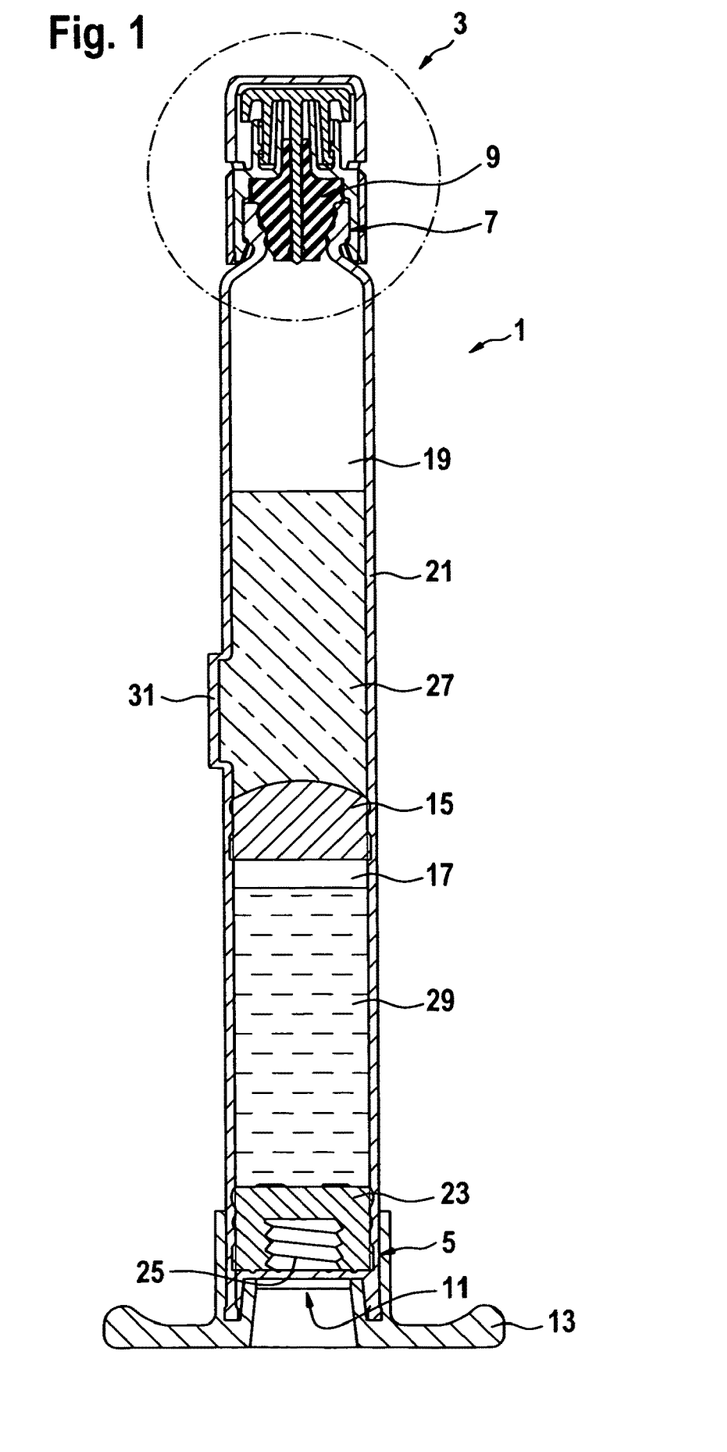
FIG. 1 is a powder syringe that is configured as a dual chamber system having a first embodiment of the closure piece.

FIG. 1 shows a powder syringe 1 provided with a representation of a first embodiment of a closure piece 3. The powder syringe 1 includes a proximal end 5 and a distal end 7. A distal opening 9 is provided on the distal end 7. A proximal opening 11 is provided on the proximal end 5. A finger rest 13 is disposed in the area of the proximal opening 5 that includes a passage for a piston rod, which is presently not shown.

In the shown embodiment, the powder syringe 1 is configured as a dual chamber system. During the production of this syringe, a central plug 15 is inserted through the proximal opening 11 into the interior of the powder syringe 1, which then divides a proximal chamber 17 from a distal chamber 19. The distal chamber 19 is preferably filled through the distal opening 9. For example, it is possible to fill in a dissolved active substance or a combination of dissolved active substances, meaning it is possible to fill in a solution that is afterwards lyophilized. Subsequently, the distal chamber 19 or the distal opening 9, respectively, is closed by means of the closure piece 3. A lyophilisate cake that is disposed in the distal chamber 19 typically adheres to a wall 21 of the powder syringe 1, such that it is not freely movable inside the distal chamber 19.

If a powder-like, soluble substance is filled into the distal chamber 19 instead, said substance is able to distribute itself freely therein. The distal chamber 19 is closed by means of a closure piece 3. The powder is then able to reach a channel region of the closure piece 3 and may form insoluble agglomerates therein. These agglomerates clog the channel and compromise the functionality of the powder syringe 1.

A solvent can be filled into the proximal chamber 17 through the proximal opening 11, and afterwards this opening is closed by means of an end plug 23. The end plug 23 preferably includes coupling means 25 for a coupled connection to a piston rod that is presently not shown. In the depicted embodiment, the coupling means 25 is an internal thread that is able to mesh with the outside thread of the piston rod, which is presently not shown.

Correspondingly, preferably a powder 27 is present in the distal chamber 19 of the powder syringe 1, which is presently configured as a dual chamber system. The proximal chamber 17 preferably contains a solvent 29. The powder 27 is preferably soluble in the solvent 29.

In the area of the distal chamber 19, the wall 21 includes a radial projection, that extends—seen in the circumferential direction—only over a relatively small angular range and that is configured as the bypass 31. To activate the dual chamber system, the end plug 23 is displaced, aided by the piston rod that is not shown, in the direction of the distal end 7. wherein, due to the pressure forces that have developed inside the proximal chamber 17, the middle plug 15 is also displaced in this direction.

The present description refers generally to a longitudinal direction that corresponds to the longitudinal extension of the powder syringe 1. A radial direction refers, correspondingly, to a direction that is perpendicular in relation to said longitudinal direction. The longitudinal direction is also referred to as the axial direction. A circumferential direction extends along a circumferential line around the longitudinal axis of the powder syringe 1.

The bypass 31 has—seen in the longitudinal direction— an extension that is larger than the axial length of the central plug 15. This is the reason why, when the central plug 15 is displaced into the bypass region 31, a fluid connection is established between the proximal chamber 17 and the distal chamber 19 via the bypass 31. The solvent 29 is then introduced, particularly by means of a further displacement of the end plug 23 from the proximal chamber 17 into the distal chamber 19, where it dissolves the powder 27. Finally a state is reached where the central plug 15 and the end plug 23 rest against each other. By a displacement of the two plugs toward the distal end 7, it is now possible for the solution, that is present in the distal chamber 19, to be expelled from the powder syringe 1, and preferably injected into a patient. The configuration and functionality of such dual chamber system is known from the prior art, which is why it will not be discussed in further detail.

In a dual chamber systems that must take up powder in the distal chambers thereof, the distal opening 9 is preferably expanded, in comparison to dual chamber systems that are envisioned for lyophilisates, because, this way, the powder filling process is facilitated, while a smaller diameter is sufficient for a solution.

The invention is not limited to powder syringes that are configured as dual chamber systems. Basically any powder syringe suffers from the problem whereby a powder, that is present inside a chamber of the syringe, can clump inside a channel of a closure piece. Correspondingly, the presently proposed solution is applicable with regard to any powder syringe. It has also been demonstrated that a lyophilisate, which is present inside the distal chamber of a dual chamber system, may pulverize at least in part over the course of the storage period, thereby acquiring the potential for clogging the channel of a closure piece. Consequently, it is understood that the proposed closure piece can be used, preferably, also in dual chamber systems that comprise a lyophilisate in the distal chambers thereof.

Figure 2:
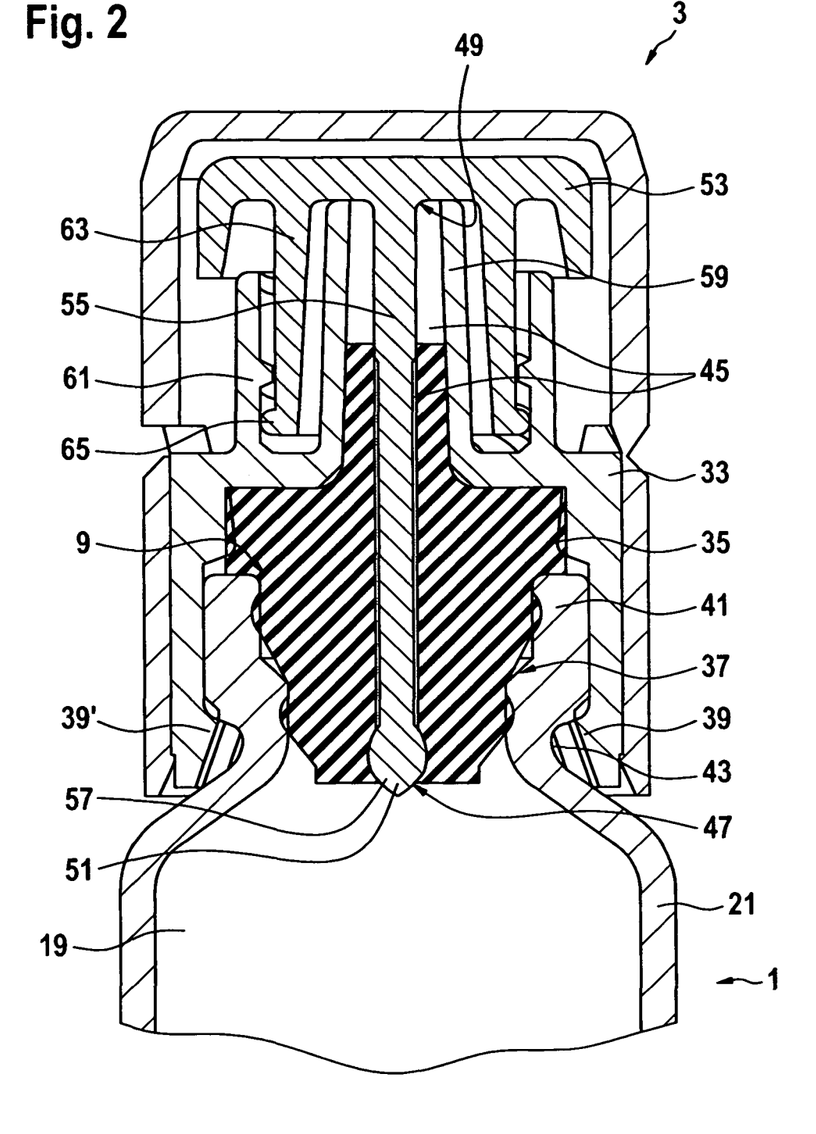
FIG. 2 is a detail view of the embodiment of a closure piece according to FIG. 1.

FIG. 2 shows a detail view of the representation of the embodiment of the closure piece 3 according to FIG. 1. Same and functionally identical elements are identified by the same reference signs, such that presently reference is made to the preceding description. The closure piece 3 includes a main body 33. A sealing element 35 is disposed thereon in such a fashion that it rests in a sealing manner against the distal opening 9 of the powder syringe 1, when the closure piece 3 is in the presently depicted closing position.

The sealing element 35 is made of an elastic material and is quasi clamped between the wall 21 of the powder syringe 1 and the main body 33 of the closure piece 3, such that there results a sealing effect. In the presently depicted embodiment, a mouth region 37 of the powder syringe 1 has an internal contour to which an external contour of the sealing element 35 is adjusted such that said element rests alongside the entire mouth region 37, when the closure piece 3 is in the closing position.

Edges of the sealing element 35 in FIG. 2 are in part depicted as overlapping with edges of the main body 33 and the wall 21. This is nothing more than an artefact in the assembly of the technical drawing, where the sealing element 35 is shown in the non-compressed state thereof between the main body 33 and the wall 21. In reality, the sealing element is compressed, then resting tightly against the main body 33 and the wall 21. Had this state been depicted realistically here, the corresponding edges would lie against each other, without overlapping.

The main body 33 includes at the end thereof that is oriented toward the distal chamber 19 the radial protrusions 39, 39', which are directed toward the inside. By said protrusions, the main body reaches behind a flange 41 of the powder syringe 1, which is provided in the mouth region 37 such that an undercut or groove 43 is quasi formed in the wall 21. In the closing position of the closure piece 3, the protrusions 39, 39' engage therein, quasi in the fashion of latch noses. This way, it is possible to introduce forces into the sealing element 35 that compress said sealing element and facilitate the tight contact position in the area of the distal opening 9 and/or in the mouth region 37. Simultaneously, the protrusions 39, 39' hold the closure piece 3 safely in place on the main body of the powder syringe 1 that is constituted by the wall 21.

If the closure piece 3 is used in connection with a lyophilisate that is provided inside the distal chamber 19, the flange 41 preferably comprises an annular-like groove that reaches around it—seen in the circumferential direction. The projections 39, 39' can also engage in a latching manner in this groove, which is presently not shown. In the view as represented in FIG. 2, as further latch position is configured quasi above the depicted latch position of the closure piece 3, and in which, not only, is the sealing element 35 not compressed but it also leaves a gap in the area of the distal opening 9, such that there is fluid communication from the distal chamber 19 to the environment of the powder syringe 1. It is possible to lyophilize a solution that is provided in the distal chamber 19, while the closure piece 3 is disposed in the top latch position thereof. After the lyophilization process is complete, the closure piece 3 is brought into the latch position as depicted in 2, from where it closes distal chamber 19 in a sealing manner.

The closure piece 3 includes a channel 45 that passes through the main body 33 and the sealing element 35. The channel 45 includes a proximal end 47 and a distal end 49.

In known closure pieces it is possible for powder-like material from the distal chamber 19 to penetrate the channel 45 via the proximal end 47. Clumping can occur at this location, and the agglomerates may be insoluble and thereby impair the functionality of the powder syringe 1.

To prevent this from occurring, the closure piece 3 includes a retaining element 51 that is configured and/or can be disposed in such a manner that, at any rate, prior to the activation of the powder syringe, no powder from the distal chamber 19 is able to penetrate the channel 45, when the closure piece 3 is disposed in the closing position on the powder syringe, as shown in FIG. 2.

In the depicted representation of the embodiment, the closure piece 3 includes a closure piece cap 53 that closes the distal end 49 of the channel 45.

The closure piece cap 53 preferably comprises a rod-like projection 55. Said projection passes through the channel. The retaining element 51 is provided on the projection 55.

For example, it is possible to configure the preferably rod-like projection 55 having a diameter that is greater than the diameter of the section of the channel 45 that passes through the sealing element 35. The sealing element 35 is then compressed, when the projection 55 is inserted in the corresponding channel section, and it rests correspondingly against the same in a sealing manner. If the projection 55 then includes an extension—seen in the longitudinal direction—that reaches all the way to the proximal end 47, the channel 45 is tightly sealed, such that no powder is able to penetrate into the channel.

It is disadvantageous, however, that, due to the friction between the projection 55 and the sealing element 35, great force is needed to remove the closure piece cap 53 in the embodiment having a rod-like projection along the totality of the longitudinal extension with a corresponding diameter.

Therefore, an embodiment where the retaining element 51 is configured as a thickening 57 of the rod-like projection is preferred. In the depicted preferred embodiment, the thickening 57 is provided on the end of the projection 55 that is oriented toward the distal chamber 19. Preferably, the projection 55 passes through the entire sealing element 35, such that it extends at least partially from the proximal end 47 of the channel 45 by the thickening 57 thereof. In the region of the thickening 57, which preferably has a greatest diameter, that is greater than the inside diameter of the section of the channel 45 that is provided on the inside of the sealing element 35, the sealing element 35 rests there-against in a sealing manner, such that the proximal end 47 is tightly sealed. No powder can therefore penetrate into the channel 45.

If a retaining element is provided in form of a thickening 57 and is part of the projection, the diameter of the projection can be configured as smaller outside of the thickening 57 than the inside diameter of the section of the channel 45 inside the sealing element 35. This causes a reduction of the frictional forces that are generated when removing the closure piece cap 53.

It is possible to configure the projection 55 as having a larger diameter in the area in which said projection exits from the sealing element 35 opposite to the proximal end 47, thereby tightly sealing the portion of the channel 45 that extends through the sealing element 35 as well. In this case, the inlet and outlet of the channel 45 to and from the sealing element 35, respectively, are tightly closed by the projection 55.

It can be discerned further based on FIG. 2 as follows: the main body 33 preferably includes a shoulder 59 that serves for the coupling action with a cannula or a needle of a syringe. In particular, it is possible to configure the shoulder 59 as tapered. A configuration as a Luer cone is especially preferred. Correspondingly, it is possible for the main body 33 to include a Luer thread 61 that reaches around the shoulder 59, serving to create a coupling with dispensing means for dispensing an active substance or a solution. Luer cones and Luer threads are known in the art and will therefore not be discussed in further detail. Preferably, the closure piece cap 53 further includes a wall section 63 that reaches around the shoulder 59. At the end thereof that is oriented toward the distal chamber 19, there is provided a radially extending projection 65—seen in the circumferential direction. Said projection is preferably engaged in the Luer thread 61, such that the closure piece cap 53 can be screwed into the Luer thread or out of the Luer thread, respectively.

Figure 3:
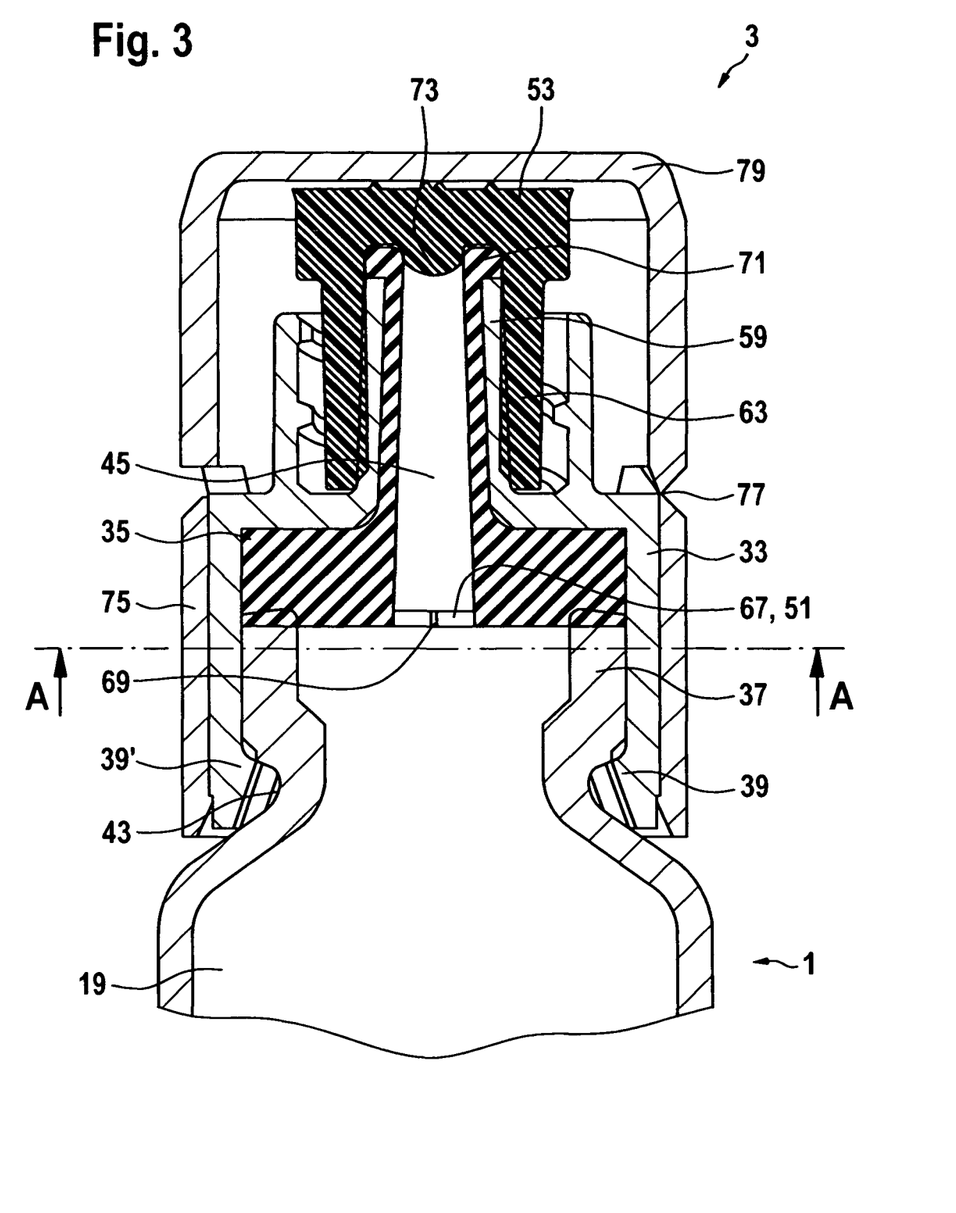
FIG. 3 is a second embodiment of a closure piece.

FIG. 3 shows a representation of a second embodiment of a closure piece 3. Same and functionally identical elements are identified by the same reference signs, such that presently reference is made to the preceding description. For better clarity, not all reference signs are reflected but only those that are directly referenced in the description. In the embodiment that is represented in FIG. 3, the retaining element is configured as a membrane 67. The membrane can be configured such that, in principle, the membrane can be perforated or torn, it can burst, particularly when it is subjected to pressure forces, or it can be destroyed in another way. Destructible membranes, particularly membranes that can be perforated or burst open, suffer from the disadvantage that small particles come loose from the membrane, when the membrane is opened, which may be injected into the patient. In the depicted embodiment, the membrane 67 is, therefore, preferably configured as a slotted membrane. This means it includes at least one slot 69, where the membrane can be dilated when pressure forces are applied. The slot can be originally formed as part of a preferably originally injection-molded membrane, meaning the slot is generated during the injection-molding process. Preferably, it is also possible to incorporate the slot after the production of the membrane, for example by means of a cutting step, preferably a laser cutting step. It is preferred that the slot is so narrow in the closed state thereof that no powder is able to penetrate through it. However, it is also possible that only such a minimal powder quantity is able to penetrate through the slot that any clumping inside the channel 45 is still precluded. An embodiment of this type also falls within the scope of protection of the subject-matter of the present invention.

In the shown representation of the embodiment, the sealing element 35 is configured as shorter—seen in the axial direction—than in the embodiment according to FIG. 2. In particular, presently, it does not include a contour that extends into the mouth region 37 and follows that contour. Similarly, it is also possible to provide a preferably slotted membrane in the context of a sealing element that is configured as shown in FIG. 2.

However, in the depicted embodiment, the sealing element 35 extends through the entire shoulder 59 of the main body 33. It even reaches over the shoulder 59—seen in the axial direction—and forms an annular support region 71 at the distal end thereof.

The closure piece cap 53 presently rests in a sealing manner, together with the wall section 63, against the shoulder 59. It only has a short central projection 73 that extends, over a comparatively short distance, into the channel 45, resting tightly against the sealing element 35.

The main body 33, and therefore also the shoulder 59, comprises material, and/or it is made of material that is typically not suited for primary contact. This means that the medication is not allowed to come into contact with the main body 33, particularly during storage. This is the reason why the closure piece cap 53 typically includes a projection 73 that extends—seen in the axial direction—at least far enough that it ends resting in a sealing manner against the sealing element 35. This way, it is avoided that a material that is provided in the distal chamber 19 comes into contact with the material of the main body 33. If the sealing element 35 extends, however, through the entire shoulder 59—as in the representation of the embodiment that is shown in FIG. 3—forming an annular support region 71 even beyond the same, it is not necessary to provide a long projection 73 on the closure piece cap 53. Instead, it is sufficient for said projection to be configured such that is engages, still in a sealing manner, with the support region 71. This way, it is ensured that any substance provided inside the distal chamber 19 will not come into contact with the material of the main body 33.

It can also be discerned as follows: in the closing position of the closure piece 3, the protrusions 39, 39' are pressed into the latch position of the groove 43 by a safety cap 79. The safety ring 75 is connected to a safety cap 79 by the tear-off bars 77, and said cap reaches over and around the closure piece cap 53. When applying the closure piece 53, the main body 33 is first displaced into the closing position thereof, subsequently, the safety ring 75 is pushed over the same by means of the safety cap 79, such that the main body 33 is ultimately safely held in the latched position thereof. To open the closure piece 3, the safety cap 79 is separated from the safety ring 75 in the area of the tear-off bars 77 and then removed. The closure piece cap 53 can then be removed to create a fluid communication between of the environment of the powder syringe 1 and the channel 45.

Figure 4:
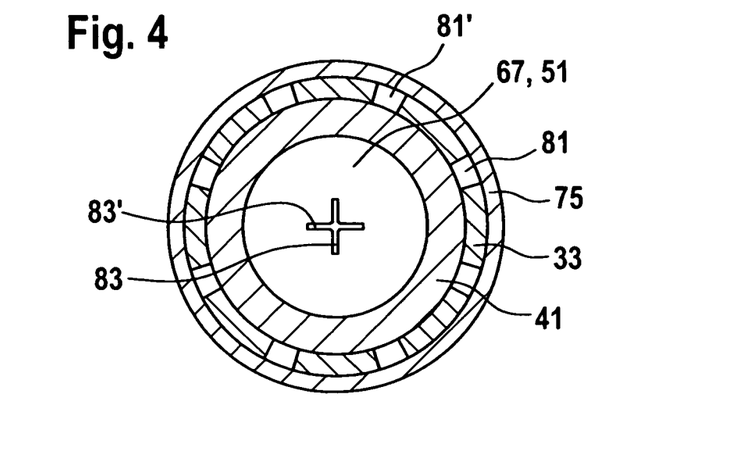
FIG. 4 is a sectional view of an embodiment according to FIG. 3 along the line A-A.

FIG. 4 is a sectional view of the embodiment according to FIG. 3 along a line A-A. Same and functionally identical elements are identified by the same reference signs, such that presently reference is made to the preceding description. The outer area shows the safety ring 75 that reaches around the main body 33. It is illustrated therein that the main body 33 includes a plurality of slots or recesses, respectively, in the area of the sectional plane, and particularly in the area of the protrusions 39, 39'—seen in the circumferential direction—that extend over a certain area—seen in the axial direction. Solely by way of an example, two slots are identified herein by the reference numerals 81, 81'. Overall, a total of eight slots or recesses, respectively, is provided in FIG. 4 along the circumference of the main body. Said recesses ensure, on the one hand, that the main body 33 has sufficient elasticity in the area of the protrusions 39, 39' to be pushed over the flange 41 prior to the protrusions 39, 39' engaging in the groove 43. On the other hand, the recesses are essential, when the closure piece 3 is used in conjunction with a dual chamber system that has a lyophilisate provided in the distal chamber 19 thereof. As previously explained, the closure piece 3 is preferably disposed in the top latch position during the lyophilization, where it does not provide a tight seal for the distal opening 9 of the dual chamber system. The fluid path that the evaporating solvent can take during the freeze-drying process from the distal chamber 19 and the distal opening 9, able to reach the environment of the dual chamber system, then follows such recesses, particularly also, as shown by way of an example, by the slots identified with the numerals 81, 81'.

The membrane 67 is disposed in the center of the representation in FIG. 4. Said membrane includes two slots 83, 83' that are perpendicular in relation to each other, such that a cross-shaped slot design is created. It is possible for the membrane 67 to have only one slot. More than two slots are conceivable as well. If two slots are provided, they do not have to be disposed at a right angle. In principle, any number and any geometric slot arrangement is possible.

The essential aspect is that the width of the slots and/or an opening that is disposed in the center of the presently crosswise arranged slot design, that includes the slots 83, 83', is smaller than the mean grain size of the powder that is provided inside the distal chamber 19. Preferably, the opening or the width of the slot, respectively, is smaller than the smallest grain size of said given powder. This way, it is ensured that the membrane 67 acts as a retaining means 51 and efficiently prevents any powder from penetrating the channel 45. When the powder syringe is activated, which means a solution that is present in the distal chamber 19 is slated for injection, the membrane 67 is dilated such that, due to the pressure forces that have developed inside the distal chamber 19, is releases a fluid path to the channel 45 at least in the area of the slots 83, 83'. It is also possible that the membrane 67 tears open, due to the effect of the pressure forces, preferably along the slots 83, 83', such that a fluid path having a larger diameter is released.

In the embodiment that is presently shown, the membrane 67 is configured in one piece with the sealing element 35. It is also possible to provide the same as a separate element. In such a case, said membrane is preferably connected to the sealing element 35 in a suitable manner. It is especially preferred that the membrane 67 is disposed on the proximal end 47 of the channel 45.

Figure 5:
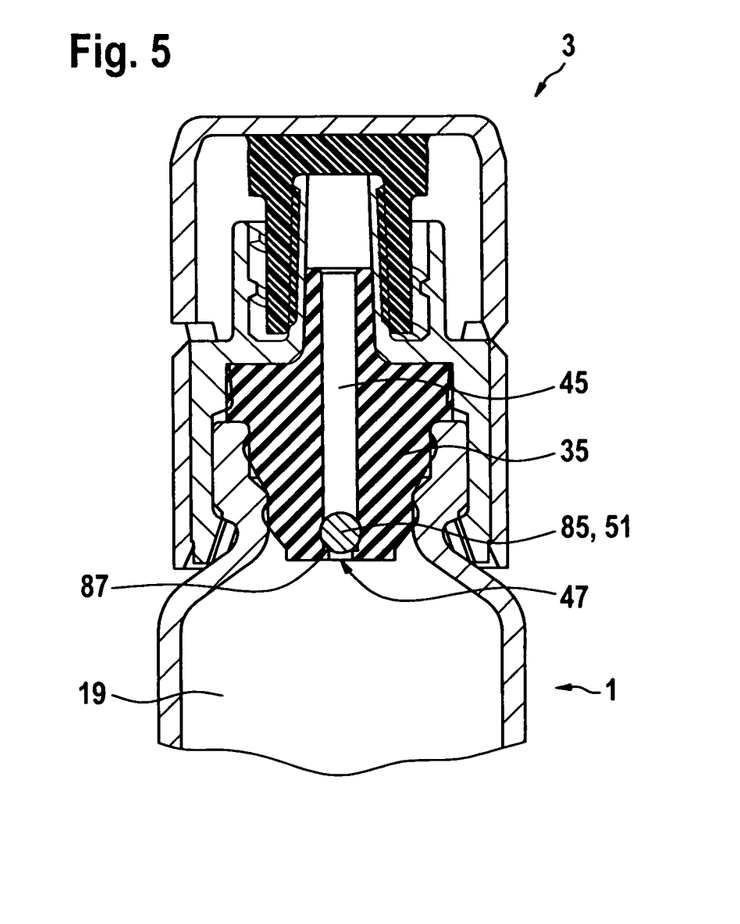
FIG. 5 is a third embodiment of the closure piece.

FIG. 5 is a representation of a third embodiment of a closure piece 3. Same and functionally identical elements are identified by the same reference signs, such that presently reference is made to the preceding description. The retaining element 51 herein is configured as an element that is displaceable along the channel 45. In the depicted embodiment, the displaceable element is a ball 85. Said ball has a diameter that is larger than the diameter of the section of the channel 45 that is disposed inside the sealing element 35. This way, it is possible to seal the proximal end 47 by means of the ball 85. Friction holds the ball 85 in the closing position thereof.

In other embodiments, the displaceable element can have a different geometry. For example, it is possible to provide at least one protrusion on the ball 85 that extends beyond the proximal end 47 and into the distal chamber 19. This way, the channel 45 can also be directly closed off at the proximal end 47. Instead of the ball 85, it is also possible to envision, for example, a cylindrical element. Said element can also include a corresponding protrusion. Any alternative geometries are possible.

The displaceable element preferably comprises glass or is made of glass. It has the necessary hardness, such that the sealing elements 35 can rest there against in a sealing manner. In addition, glass is a suitable primary contact material.

In the depicted representation of the embodiment, a holding means 87 is provided for the displaceable element on the proximal end 47. Said holding means prevents the displaceable element from penetrating the distal chamber 19. The holding means 87 is configured as a radial protrusion from a wall of the channel 45 in the represented embodiment against which the ball 85 comes to rest. If the displaceable element includes a protrusion, said protrusion can also extend through the area of the holding means 87, such that this region is protected against any penetrating powder from the distal chamber 19. A residual volume of the channel 45, where clumping could still occur, is not only minimized in this manner but substantially prevented, or completely altogether.

When pressure forces are introduced into the distal chamber 19 to activate the powder syringe 1, the displaceable element moves inside the channel 45 and away from the distal chamber 19. Finally, it exits from the channel at the distal end 49 thereof.

It is disadvantageous herein that the displaceable element is then either flushed from the powder syringe 1, wherein, in the worst case scenario, it is injected into a patient, or it blocks a cannula or a needle of a syringe and/or closes off the inlet thereto. Therefore, a retaining means is preferably provided for retaining said displaceable element while, simultaneously, releasing a fluid path in the environment of the powder syringe 1. A retaining means of this kind can be provided in a specially manufactured cannula attachment. However, this is, comparatively speaking, a complex and expensive solution, because it is not possible, if this is done, to use the closure piece 3 or the powder syringe 1 in conjunction with conventional cannulas and/or syringe needles.

Figure 6:
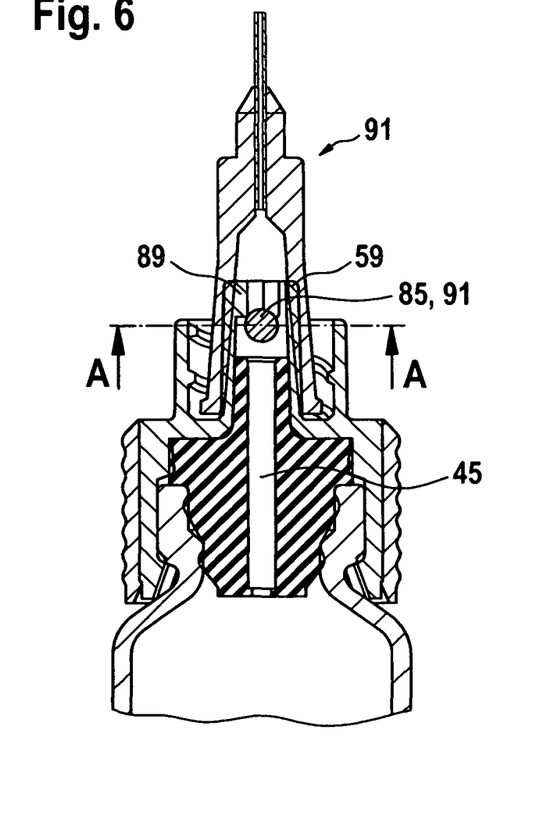
FIG. 6 is a slight variation of an embodiment with regard to FIG. 5 of a closure piece on a powder syringe in the activated state.

FIG. 6 shows a representation of an embodiment that is a slight variation of the embodiment of the closure piece 3 in the activated state as depicted in FIG. 5. Same and functionally identical elements are identified by the same reference signs, such that presently reference is made to the preceding description. A retaining means 89 for the displaceable element is presently provided in the area of the distal end 49 of the channel 45. A cannula 91 is disposed on the shoulder 59. Said cannula preferably comprises an internal cone that is able to function in conjunction with a shoulder 59, which is preferably configured as tapered, such that a tight connection is ensured from the powder syringe 1 to the cannula 91. The retaining means 91 quasi catches the displaceable element. Simultaneously, however, the fluid path from the channel 45 to the cannula 91 remains intact. In particular, an injection solution is able herein to circumflow the displaceable element that is presently configured as a ball 85.

Figure 7:
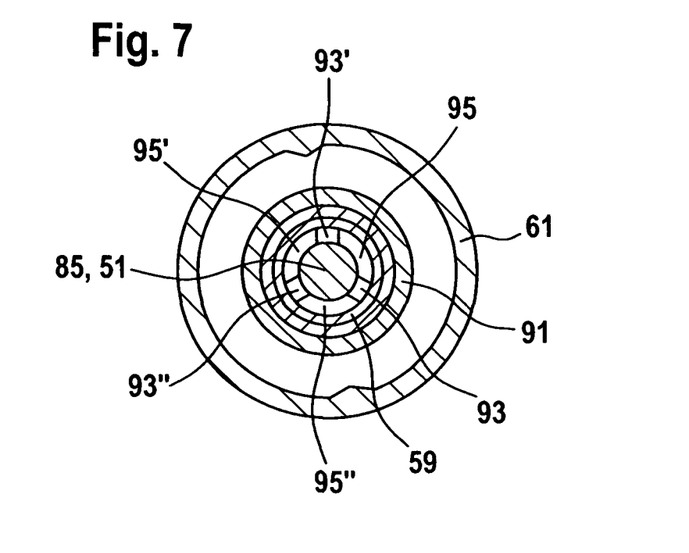
FIG. 7 is a sectional view of an embodiment according to FIG. 6 along the line A-A.

The functionality of the retaining means 89 is explained in further detail based on the sectional view as depicted in FIG. 7 along a line A-A in FIG. 6. Same and functionally identical elements are identified by the same reference signs, such that presently reference is made to the preceding description. The Luer thread 61 is depicted in the outer region of FIG. 7. Toward the inside—seen in the radial direction—then follows a wall section of cannula 91. Further radially inside, the shoulder 59 is finally shown. Again, there appears to be overlap that is the result of fact that the state of assembly of the elements in the drawing was drawn based on the disassembled configuration thereof. Any dilation or compression of materials occurring during the assembly of the different elements was presently not taken into consideration, which is why there seem to be overlaps in some regions.

In the area of the distal end 49, the shoulder 59 includes the radial protrusions 93, 93', 93''' that project deeply enough into the channel 45 for retaining the displaceable element or the ball 85, respectively. Three radial protrusions 93, 93', 93" are provided in the depicted representation of the embodiment—seen in the circumferential direction. A single radial protrusion is ultimately sufficient if it radially extends far enough to the inside to be able to retain the ball 85. Two or more than three protrusions are possible as well. The essential aspect—seen in the circumferential direction—is that the free spaces 95, 95', 95" are preserved, which will allow for a fluid communication between the channel 45 and an environment of the powder syringe 1 or the cannula 91, respectively. An injection solution is thus able to flow around the ball 85 or the displaceable element, respectively, exit the channel 45 through the free spaces 95, 95', 95" and enter the environment of the powder syringe 1 or the cannula 91, respectively.

Figure 8:
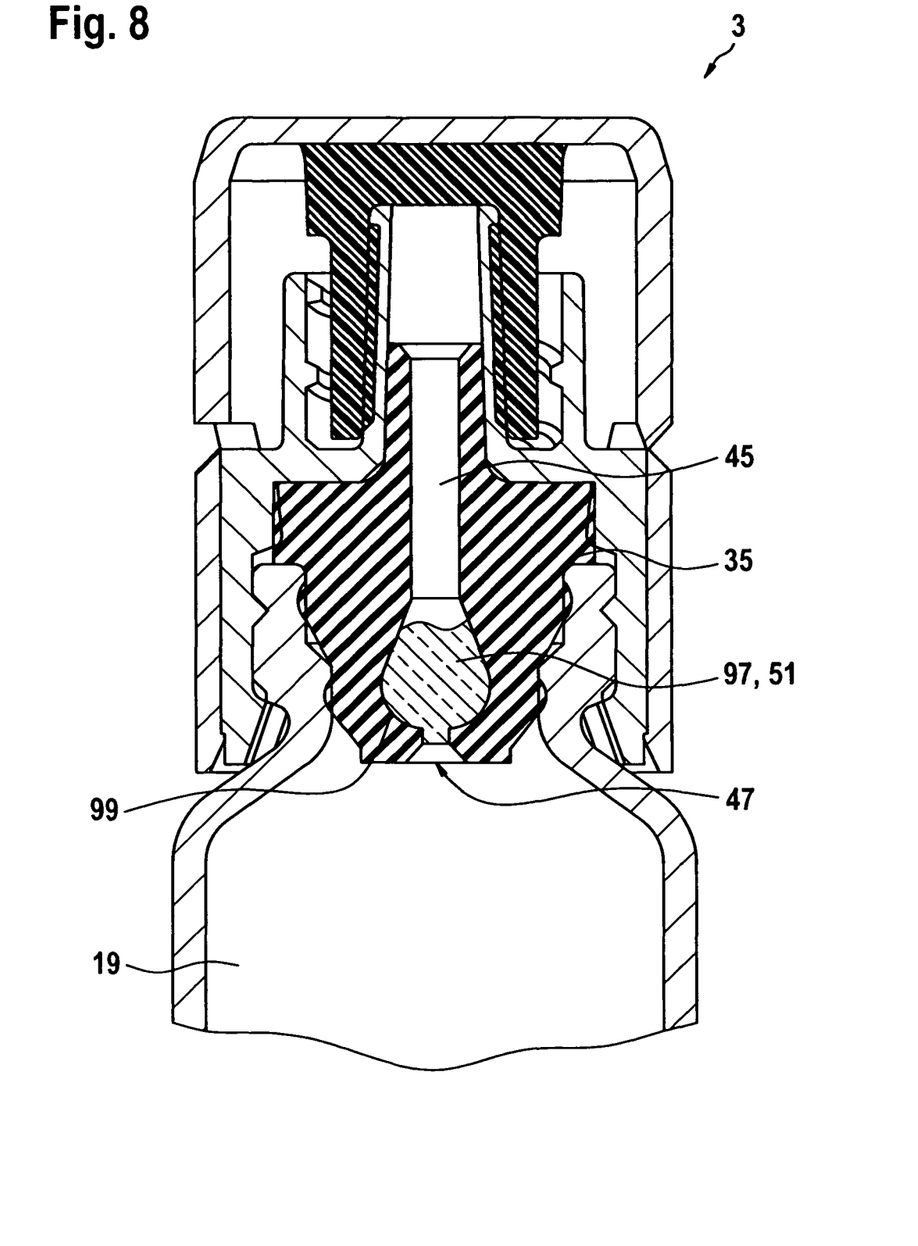
FIG. 8 is a fourth embodiment of a closure piece.

FIG. 8 is a representation of a fourth embodiment of the closure piece 3. Same and functionally identical elements are identified by the same reference signs, such that presently reference is made to the preceding description. The retaining element herein comprises a soluble substance 97. Said substance is selected in such a manner that it is soluble in the same solvent as the powder, or possibly the lyophilisate, which must be dissolved and that is present in the distal chamber 19. It is particularly preferred when the soluble substance 97 is a lyophilized substance. Using a device, which is presently not shown, it is possible to bring the solution into the sealing element 35 and lyophilize said solution therein in order to form a lyophilisate cake that blocks the channel 45.

In the depicted preferred embodiment, an extension 99 is provided in the region of the proximal end 47 for receiving the substance 97. It quasi forms a plug that blocks the channel 45 and thereby prevents the powder, which is present in the distal chamber 19, from penetrating into the channel.

Figure 9:
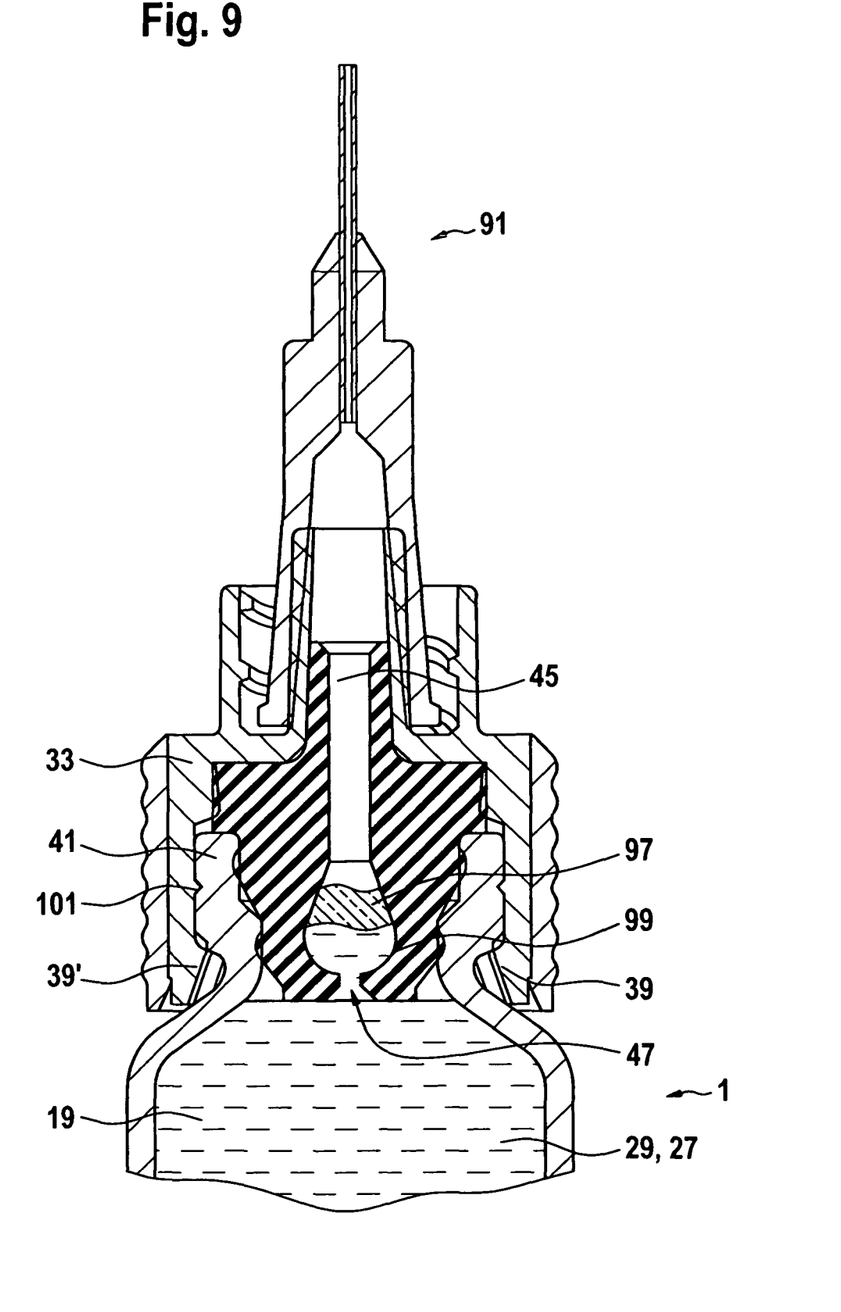
FIG. 9 is the embodiment according to FIG. 8 in the activated state.

The functionality of this embodiment will be illustrated in further detail based on FIG. 9. Same and functionally identical elements are identified by the same reference signs, such that presently reference is made to the preceding description. When the powder syringe 1 is activated, the solvent 29 reaches the distal chamber 19. Inside said chamber, the powder 27 is dissolved in the solvent 29. The solution then reaches the extension 99 via the proximal end 47, where the substance 97 is present. Due to the fact that said substance is also soluble in the solvent 29, it is dissolved, as shown in FIG. 9. This means that the plug, which had blocked the channel 45 gradually dissolves, such that finally the fluid connection from the distal chamber 19 to the channel 45 has been released. In the end, the injection solution can be conveyed to the cannula 91 and from there into a patient.

It is possible for the substance 97 to comprise excipients such as, for example, vitamin C. In addition, it is possible to add to the active substance, which is present in the distal chamber 19, further excipients that are quasi-supplied by the auxiliary substance 97, which is provided as retaining element 51.

Preferably, the substance 97 can also be incorporated in the sealing element 35 as a pellet, preferably in the extension 99. If this is the case, the additional lyophilization step for the substance 97 can be omitted.

Based on FIG. 9, it can be further discerned as follows: by way of an example, a ring groove 101 is shown in the area of the flange 41, and the protrusions 39, 39' of the main body 33 engage therein in the top latch position thereof, when a substance is lyophilized in the distal chamber 19.

Figure 10:
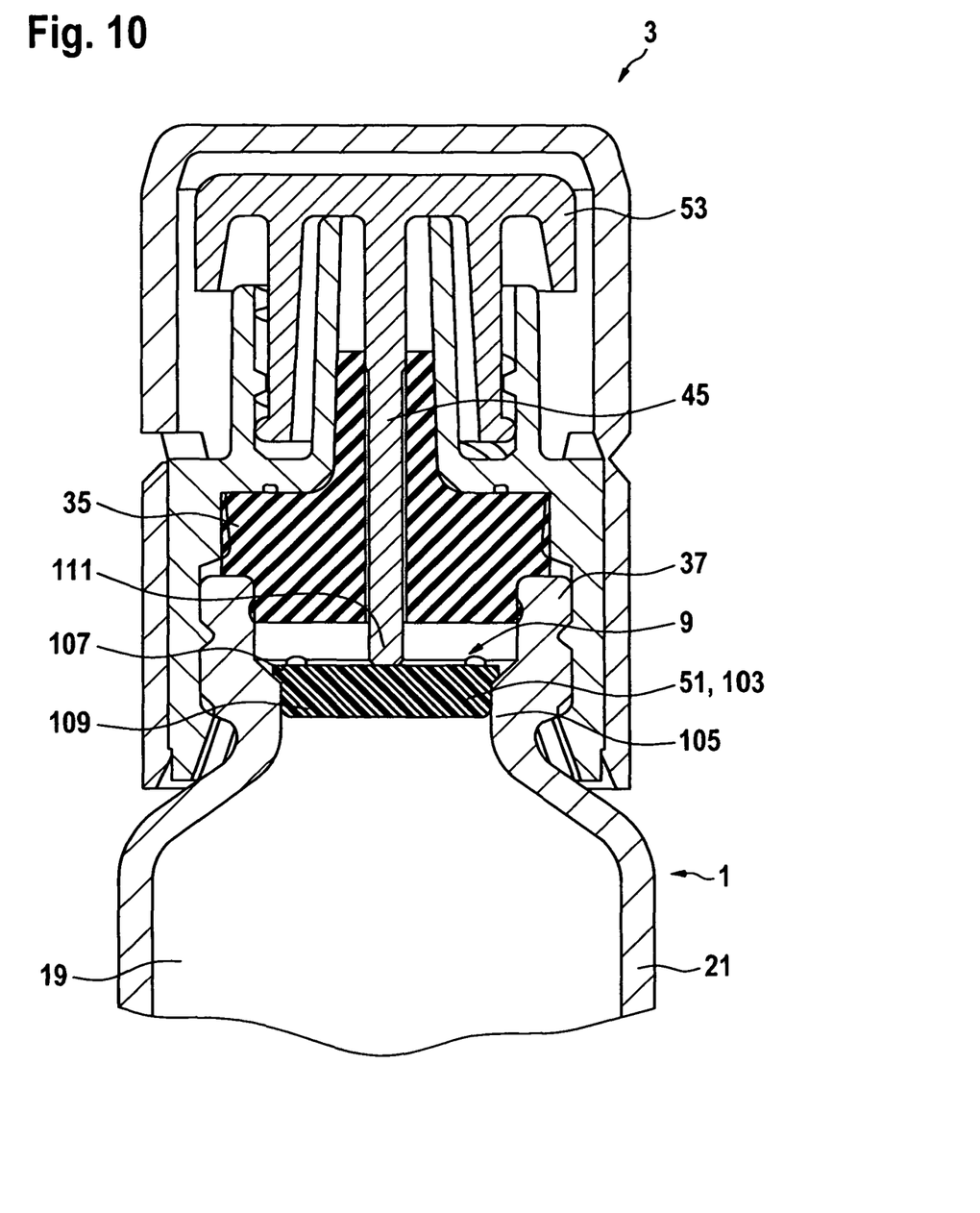
FIG. 10 is a fifth embodiment of a closure piece.

FIG. 10 is a representation of a fifth embodiment of the closure piece 3. Same and functionally identical elements are identified by the same reference signs, such that presently reference is made to the preceding description. The retaining element 51 herein comprises a closure piece disc 103. The closure piece disc can be disposed in such a manner that it closes the distal chamber 19, such that no powder is able to enter the channel 45.

The powder syringe 1 preferably comprises a narrowing 105 in the mouth region 37. In this area, the wall 21 jumps radially to the inside, such that the narrowing 105 is formed. Preferably, the closure piece disc 103 is constituted such that it is able to rest in a sealing manner against the narrowing 105. To this end, it preferably includes a radially extending protrusion 107—seen in the circumferential direction. In a region 109—seen in the axial direction—following the protrusion 107, the closure piece disc 103 preferably has an outside diameter that corresponds to the inside diameter of the narrowing 105. Correspondingly, the external contour of the closure piece disc 103 quasi follows the internal contour of the narrowing 105 or of the mouth region 37, respectively, such that it rests by the protrusion 107 and the region 109 in a sealing manner against the wall 21.

In the depicted embodiment as well, the closure piece cap 53 preferably includes a rod-like protrusion that is presently configured as a safety pin 111 and that passes through the channel 45. With an applied closure piece cap 53, said pin rests in the closing position of the closure piece 3 against the closure piece disc 103 and holds the same in a sealing contact against the narrowing 105.

The narrowing 105 is preferably provided in the area of the distal end 9 of the powder syringe 1.

The closure piece disc 103 is preferably comprised of rubber or TPE; it is especially preferred when it is made of at least one of these materials. In that case, it has good sealing properties; moreover, the named materials are suitable for primary contact.

Figure 11:
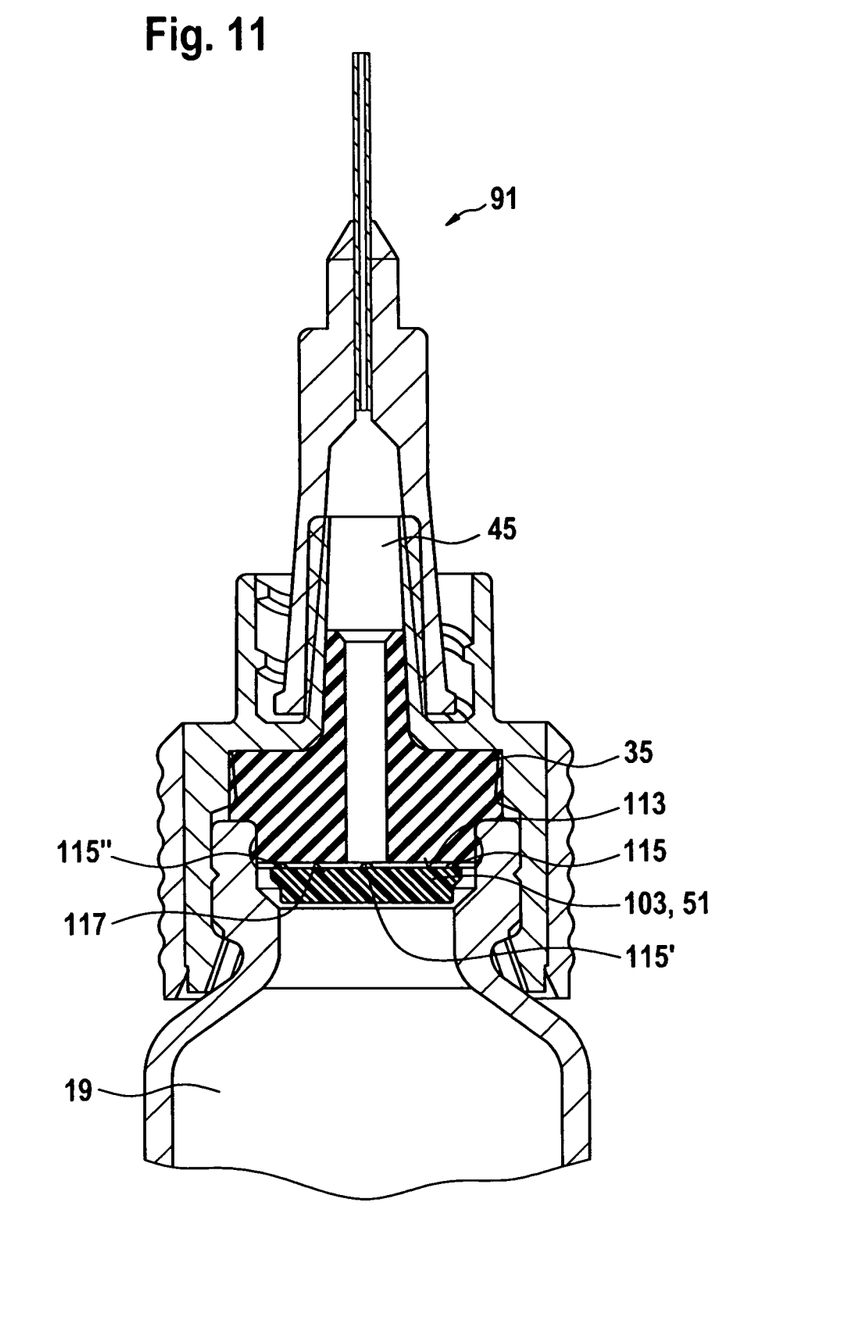
FIG. 11 is the embodiment according to FIG. 10 in activated state.

FIG. 11 is a representation of an embodiment according to FIG. 10 in the activated state. Same and functionally identical elements are identified by the same reference signs, such that presently reference is made to the preceding description. To activate the powder syringe 1, first the closure piece cap 53 and thereby the safety pin 111 are removed. Afterwards, a pressure is generated inside the distal chamber 19 that pushes the closure piece disc 103 toward the sealing element 35. Said disc includes on a surface 113, which is oriented toward the sealing element 35, at least one protrusion, presently these are three protrusions 115, 115', 115". By these protrusions, the disc supports itself against the counter-surface 117 of the sealing element 35. Correspondingly, due to the protrusion 115, the surface 113 and the counter-surface 117 are held at a distance relative to each other, such that a fluid path is formed between the same and the protrusions 115, 115', 115". The solution that exits from the distal chamber 19 is thus able to flow around the closure piece disc 103 and enters the channel 45. From there, it can be dispensed to the cannula 91.

Overall, it can be discerned that the presently proposed closure piece and the presently proposed powder syringe prevent any clumping risk inside the channel 45 by providing the retaining element 51. This translates into a considerable contribution to the improvement of the shelf-life of powder syringes, particularly of powder syringes with a dual chamber system, thereby ensuring the functionality of powder syringes even after long storage periods.

The invention claimed is:

1. A closure piece for a powder syringe comprising:
   a main body;
   an elastic sealing element disposed on the main body and resting in a sealing manner against a distal opening of the powder syringe between the main body and a wall of the powder syringe when the closure piece is disposed on the powder syringe in a closing position thereof;

a channel passing through the main body and the sealing element, the channel having a proximal end and a distal end;
a closure piece cap having a projection passing through the channel; and
a retaining element for at least substantially preventing powder coming from a chamber of the powder syringe from penetrating the channel when the closure piece is disposed in the closing position on the powder syringe, the retaining element being a closure piece disc configured to rest in a sealing manner against a narrowing of the powdered syringe to prevent the powder from penetrating into the channel, wherein the projection holds the closure piece disc in a sealing contact with the powder syringe when the closure piece is in the closing position.

2. The closure piece according to claim 1, wherein the projection includes a rod-like portion passing through the channel of the sealing element, the closure piece disc proximate an end of the rod-like portion.

3. The closure piece according to claim 1, wherein the closure piece disc includes a radially extending protrusion.

4. The closure piece according to claim 1, wherein the closure piece disc has at least one protrusion on a surface that is oriented toward the sealing element.

5. The closure piece according to claim 1, wherein the closure holds the closure piece disc in a sealing contact with the powder syringe when the closure piece is in the closing position.

6. The closure piece according to claim 1 in combination with the powder syringe.

7. The combination of claim 6, wherein the powder syringe is configured as a dual chamber system.

8. The closure piece according to claim 1, wherein the projection extends in an axial direction and further wherein the closure piece disc is spaced from the sealing element in the axial direction when in the closing position.

9. The closure piece according to claim 1, wherein the elastic sealing element has an outside diameter corresponding to an inside diameter of a narrowing of the powder syringe.

10. The closure piece according to claim 1, wherein the closure piece disc is movable toward the elastic sealing element in response to a pressure generated within the powder syringe.

11. A closure piece for a powder syringe comprising:
a main body;
an elastic sealing element disposed on the main body and resting in a sealing manner against a distal opening of the powder syringe when the closure piece is disposed on the powder syringe in a closing position thereof;
a channel passing through the main body and the sealing element, the channel having a proximal end and a distal end;
a closure piece cap for closing the distal end of the channel; and
a retaining element being a closure piece disc for resting against a narrowing of the powder syringe when the closure piece is in the closing position;
wherein the closure piece cap includes a rod-like portion passing through the channel and the closure piece cap holds the closure piece disc in the closing position, and
wherein the elastic sealing element has an outside diameter corresponding to an inside diameter of a narrowing of the powder syringe.

12. The closure piece according to claim 11, wherein the closure piece disc carried at an end of the rod-like portion.

13. The closure piece according to claim 11, wherein the closure piece disc includes a radially extending protrusion.

14. The closure piece according to claim 11, wherein the closure piece disc has at least one protrusion on a surface that is oriented toward the sealing element.

15. The closure piece according to claim 11, wherein the closure holds the closure piece disc in a sealing contact with the powder syringe when the closure piece is in the closing position.

16. The closure piece according to claim 11 in combination with the powder syringe.

17. The combination of claim 16, wherein the powder syringe is configured as a dual chamber system.

18. A closure piece for a powder syringe in combination with the powder syringe, the powder syringe including a distal opening and a narrowing proximate the distal opening, the closure piece comprising:
a main body;
an elastic sealing element disposed on the main body and resting in a sealing manner against the distal opening of the powder syringe when the closure piece is disposed on the powder syringe in a closing position;
a channel passing through the sealing element, the channel having a proximal end and a distal end;
a closure piece cap for closing a distal end of the channel; and
a closure piece disc disposed within the powder syringe and resting against the narrowing of the powder syringe when the closure piece is in the closing position;
wherein the closure piece cap includes a rod-like projection passing through the channel and the closure piece cap holds the closure piece disc in the closing position, and
wherein the elastic sealing element has an outside diameter corresponding to an inside diameter of a narrowing of the powder syringe.

19. The combination according to claim 18, wherein the closure piece disc is spaced from the sealing element in the closing position.

20. The combination according to claim 18, wherein the closure piece disc includes a radially extending protrusion.

21. The combination according to claim 18, wherein the closure piece disc has at least one protrusion on a surface that is oriented toward the sealing element.

22. The combination according to claim 18, wherein the main body includes a lower portion circumferentially surrounding a distal end of the powder syringe.

23. The combination of claim 18, wherein the powder syringe is configured as a dual chamber system.

* * * * *